United States Patent
Bach et al.

(10) Patent No.: US 7,175,811 B2
(45) Date of Patent: Feb. 13, 2007

(54) MICRO-ARRAY EVANESCENT WAVE FLUORESCENCE DETECTION DEVICE

(75) Inventors: David Bach, Ellicott City, MD (US); Bruce L. Booth, Westchester, PA (US); James C. Richards, Sudbury, MA (US)

(73) Assignee: Edgelight Biosciences, Sudbury, MA (US)

( * ) Notice: Subject to any disclaimer, the term of this patent is extended or adjusted under 35 U.S.C. 154(b) by 0 days.

(21) Appl. No.: 09/845,489

(22) Filed: Apr. 30, 2001

(65) Prior Publication Data

US 2002/0110839 A1    Aug. 15, 2002

Related U.S. Application Data

(60) Provisional application No. 60/200,574, filed on Apr. 28, 2000.

(51) Int. Cl.
*G01N 21/01* (2006.01)
(52) U.S. Cl. .............. 422/82.11; 422/57; 422/80.05; 422/82.03; 436/518; 356/440; 356/246; 385/123; 385/126; 385/130; 385/30
(58) Field of Classification Search ............... 436/518; 422/57, 82.5, 82.03; 385/123, 130, 126, 385/30; 356/440, 246
See application file for complete search history.

(56) References Cited

U.S. PATENT DOCUMENTS

| | | | |
|---|---|---|---|
| 4,752,115 A * | 6/1988 | Murray et al. ............... 385/12 |
| 5,120,131 A | 6/1992 | Lukosz ..................... 356/351 |
| 5,402,514 A * | 3/1995 | Booth et al. ............... 385/130 |
| 5,430,813 A | 7/1995 | Anderson et al. ............ 385/12 |
| 5,444,807 A * | 8/1995 | Liu ........................... 385/125 |
| 5,512,492 A | 4/1996 | Herron et al. .............. 436/518 |
| 5,677,196 A | 10/1997 | Herron et al. .............. 436/518 |
| 5,736,257 A | 4/1998 | Conrad et al. ............ 428/474.4 |
| 5,785,874 A | 7/1998 | Eda .............................. 216/24 |

(Continued)

FOREIGN PATENT DOCUMENTS

WO    WO 00/09757    2/2000

OTHER PUBLICATIONS

Emmanuel Delamarche, Andre Bernard, Heinz Schmid, Bruno Michel, Hans Biebuyck Patterned Delivery of Immunoglobulins to Surfaces Using Microfluidic Networks 276 Science 779-781, 1997.*

(Continued)

*Primary Examiner*—Long V. Le
*Assistant Examiner*—Jacob Cheu
(74) *Attorney, Agent, or Firm*—Clifford Kraft (57) ABSTRACT

Novel nanowell microarrays are disclosed in optical contact with polymer waveguides wherein evanescent field associated with lightwaves propagated in the waveguide excite target substances in the nanowells either by a common waveguide or by individual waveguides. Fluid samples are conveyed to the nanowells by means of microfluidics. The presence of the target substances in fluid samples is detected by sensing fluorescent radiation generated by fluorescent tag bound to the target substances. The fluorescent tags generate fluorescent radiation as a result of their excitation by the evanescent field. One or more PMT detectors or a CCD detector are located at the side of the waveguide opposite to the nanowells. Fluorescent radiation is detected due to its coupling with the waveguide or its emission through the waveguide.

5 Claims, 5 Drawing Sheets

U.S. PATENT DOCUMENTS

| | | | | |
|---|---|---|---|---|
| 5,814,565 | A | 9/1998 | Reichert et al. | 422/82.11 |
| 5,827,748 | A | 10/1998 | Golden | 436/527 |
| 5,832,165 | A | 11/1998 | Reichert et al. | 385/130 |
| 5,835,645 | A * | 11/1998 | Jorgenson et al. | 385/12 |
| 5,846,842 | A | 12/1998 | Herron et al. | 436/518 |
| 5,862,276 | A * | 1/1999 | Karras | 385/30 |
| 5,903,685 | A | 5/1999 | Jones et al. | 385/12 |
| 5,907,408 | A | 5/1999 | Naya et al. | 365/445 |
| 5,919,712 | A | 7/1999 | Herron et al. | 436/518 |
| 5,959,292 | A | 9/1999 | Duveneck et al. | 250/227.11 |
| 5,961,924 | A | 10/1999 | Reichert et al. | 422/82.11 |
| 6,110,749 | A | 8/2000 | Obremski et al. | 436/527 |
| 6,192,168 | B1 | 2/2001 | Feldstein et al. | 385/12 |
| 6,210,910 | B1 * | 4/2001 | Walt et al. | 435/7.32 |
| 6,222,619 | B1 * | 4/2001 | Herron et al. | 356/39 |
| 6,485,690 | B1 * | 11/2002 | Pfost et al. | 422/102 |

OTHER PUBLICATIONS

Vo-Dinh, T., et al. "Evaluation of the Fiber-Optic Antibody-Based Fluoroimmunosensor for DNA Adducts in Human Placenta", Clinical Chemistry, pp. 532-535, 1991.

Ogert et al., "Detection of Clostridium botulinum Toxin A using a fiber optic-based biosenser", Analytical Biochemistry, 205, 306-312, 1992.

Shriver-Lake et al., "A fiber-optic evanescent wave immunosensor for large molecules", Sensors and Actuators B, 11, pp. 239-243, 1993.

Anderson, et al., "A fiber optic biosensor: combination tapered fibers designed for improved signal acquisition", Biosensors & Bioelectronics, 8, pp. 249-256, 1993.

Conrad et al., "Photoactivatable silanes for the site-specific immobilization of antibodies", Center for Biomolecular Science and Engineering, GEO-CENTERS, Inc., American Society for Engineering Education, pp. 1-11, 1997.

Wadkins et al., "Detection of multiple toxic agents using a planar array immunosensor", Biosensors & Bioelectronics, vol. 13, No. 3-4, pp. 407-415, 1998.

Ligler et al., "Array biosensor for multi-analyte sensing", SPIE, vol. 3258, pp. 50-55, 1998.

King et al., "Detecting staphylococcal enterotoxin B using an automated fiber optic biosensor", Biosensors & Bioelectronics 14, pp. 163-170, 1999.

Rowe et al., "An array Immunosensor for simultaneous detection of clinical analytes", Analytical Chemistry, vol. 71, No. 2, pp. 433-439, 1999.

Rowe, et al., "Array biosensor for simultaneous identification of bacterial, viral, and protein analytes", Analytical Chemistry, vol. 71, No. 17, pp. 3846-3852, 1999.

Feldstein, et al., "Array Biosensor: Optical and Fluidics Systems", Journal of Biomedical Microdevices, 1:2, pp. 139-153, 1999.

Vo-Dinh, Tuan, et al., "Biosensors and biochips: advances in biological and medical diagnostics", Fresenius J. Anal Chem, 366, pp. 540-551, 2000.

Lakowicz, J., "Fluorescence Sensing", Chapter 19 in Principles of Fluorescence Spectroscopy, Kluwer Academic/Plenum Publishers, pp. 531-572, 1999.

Biosde, G. et al., "Introduction: Historical Perspective", Chapter 1 in Chemical and Biochemical Sensing with Optical Fiber and Waveguides, Artech House Publishers, pp. 1-12, 1996.

Boisde, G., et al., "Kinetics and Shape Recognition", Chapter 3 in Chemical and Biochemical Sensing with Optical Fiber and Waveguides, Artech House Publishers, pp. 41-62, 1996.

Boisde, G. et al., "Essential Theory of Optics", Chapter 6 in Chemical and Biochemical Sensing with Optical Fiber and Waveguides, Artech House Publishers, pp. 143-172, 1996.

Boisde, G., et al., "Optical Fibers and Planar Waveguides", Ch. 7 in Chemical and Biochemical Sensing with Optical Fiber and Waveguides, Artech House Publishers, pp. 173-197, 1996.

Boisde, G., et al., "Optical Measurement Techniques", Ch. 8 in Chemical and Biochemical Sensing with Optical Fiber and Waveguides, Artech House Publishers, pp. 199-241, 1996.

Boisde, G., et al., "Optodes and Sensing Cells", Ch. 10 in Chemical and Biochemical Sensing with Optical Fiber and Waveguides, Artech House Publishers, pp. 259-284, 1996.

Boisde, G., et al., "Part IV: Applications-Biochemical Sensors and Biosensors", Ch. 11 in Chemical and Biochemical Sensing with Optical Fiber and Waveguides, Artech House Publishers, pp. 285-337, 1996.

* cited by examiner

MICRO-ARRAY EVANESCENT WAVE FLUORESCENCE DETECTION DEVICE

RELATED APPLICATIONS

This application claims the priority filing benefit of U.S. provisional patent application 60/200,574, filed on Apr. 28, 2000, which is incorporated herein by reference.

FIELD OF THE INVENTION

The present invention relates generally to the detection of molecules, such as biological molecules. More specifically, the invention relates to the system and method of detecting biological molecules bound to an array of micro wells provided in and optically associated with a waveguide. The evanescent wave created by the electromagnetic radiation propagating in the waveguide interacts with the fluorescent or other tags bound to the molecules, generating emitted fluorescent or other signal and allowing the detection of the biological molecules.

BACKGROUND OF THE INVENTION

Life science research has been undergoing a transition in recent years to large-scale experimentation, where a single project can require hundreds or thousands of measurements. Two fields that exemplify this trend are genomics and pharmaceutical drug screening. Researchers engaged in these fast growing areas need new and improved analytical systems that provide at least a ten-fold increase in the amount of data gathered as well as enhanced accuracy in the measurement of this data. To gain market acceptance, new products and systems also need to offer these benefits at attractive cost levels.

Genomics is the analysis of nucleic acids, which are the fundamental regulatory molecules of life. Nucleic acids take two forms, DNA and RNA. These molecules contain and convey the instructions that govern all cellular activities, including protein manufacture and cell reproduction. DNA and RNA consist of linear strands of nucleotide bases, commonly known as A's, G's, T's and C's, the specific sequences of which constitute the genetic information in the cell. The unique genetic blueprint for all living organisms, from bacteria to human beings, is encoded in the DNA. The entire DNA content of an organism is known as its genome, which is organized into functional units called genes. For a cell to read the genetic blueprint, the genetic information encoded in the DNA must first be copied to a specific type of RNA called messenger RNA or mRNA. The mRNA transmits this information throughout the cell and acts as the template for protein production. Proteins carry out the cellular functions encoded in the RNA copy of the DNA. Any defect or mutation in the sequence of nucleotide bases in the DNA or RNA can disrupt cell or protein function and lead to disease.

Genomics has created opportunities to fundamentally alter the field of human medicine through the discovery and development of novel drugs and an improved ability to diagnose and manage disease. Interest in understanding the relationships between genes and disease has generated a worldwide effort to identify and sequence the genes of many organisms, including the approximately three billion nucleotide pairs and the estimated 100,000 genes within the human genome. Once researchers identify the genes and their nucleotide sequences, it is anticipated that an understanding of the specific function of each of these genes and the role that different genes play in disease will require many years of additional research. Genomics also has applications in fields outside of human health care. For example, an improved understanding of plant and animal genomes will help to improve yields and productivity in the agriculture and livestock industries. The analysis of nucleic acids is also becoming increasingly important for industrial applications such as the testing of food, water and air.

The methods of analysis in the field of genomics generally fall into one of three major categories:

DNA Sequencing. DNA sequencing is the process of determining the linear order of nucleotide bases in a DNA fragment.

Genotyping. Genotyping refers to the identification of common variations in a sequence of DNA within a particular genome.

Gene Expression Analysis. Gene expression analysis involves measuring the expression of one or more genes in a specific cell or tissue.

Researchers today are utilizing all of these genomic analysis methods to understand genes, their function and genetic variability.

DNA sequencing is the process of determining the linear order of nucleotide bases in a strand of DNA and is performed with a laboratory instrument called a DNA sequencer. DNA sequencers use a technique known as electrophoresis, which uses an electric current to separate DNA molecules by size. This technique is also known as electrophoretic separation. In a DNA sequencer, the electric current causes smaller DNA molecules to move rapidly and larger DNA molecules to move more slowly. This enables the separation and ordering of complex mixtures of DNA molecules according to size, and thus allows the identification of the order of nucleotide bases.

Prior to beginning the DNA sequencing process, researchers typically must prepare the DNA samples. Preparation of a DNA sample for analysis includes manual and time-consuming laboratory processes such as centrifugation, filtration, measuring, mixing and dispensing. It is believed that sample preparation currently represents a major component of the time, labor and cost in sequencing. In addition, the manual nature of these steps renders sample preparation prone to human error, which can compromise the quality of information obtained from the sample. It is anticipated that integration and automation of these complex steps in a miniaturized format would significantly reduce the costs of sample preparation and improve data quality.

After sample preparation, researchers often analyze samples using one of the two leading types of DNA sequencers: gel-based sequencers and capillary array sequencers.

Gel-Based Sequencers. Until recently, all DNA sequencers used thin gels layered between two glass plates for performing electrophoresis. The throughput of a DNA sequencer is the number of DNA samples processed by the sequencer in a given amount of time. Throughput is determined by the time required for the electrophoretic separation and the number of DNA samples processed at one time. With early-generation DNA sequencers, the electrophoresis separation required 12 hours or longer and was limited to only 24 samples at a time.

Advanced generations of gel-based sequencers have reduced this separation time to approximately four hours and have allowed up to 96 samples to be processed at one time. While the throughput has increased with successive generations of gel-based sequencers, a significant amount of labor is still required to operate a gel-based sequencer. The labor involved in gel-based sequencers includes the time consuming tasks of preparing a new gel for each separation, loading each DNA sample onto the gel and cleaning the system after each separation.

Capillary Array Sequencers. In recent years, a number of companies have introduced a new generation of DNA sequencers, based on capillary electrophoresis. With capillary electrophoresis, each DNA sample is separated within a capillary, which is a small glass tube with the diameter of a human hair. In capillary array sequencers, up to 100 capillaries are bundled together to process many DNA samples simultaneously. Capillary array sequencers automate many of the labor-intensive steps in gel electrophoresis and provide significant improvements in operational efficiency. The time required for electrophoresis in a capillary array sequencer, however, is similar to that of current gel-based sequencers.

Advances in the performance of DNA sequencers generally have helped to rapidly expand the market for sequence information. In particular, the throughput of DNA sequencers has increased significantly over the last decade. This increase in throughput, along with improved automation, has substantially reduced the cost per unit of information obtained from DNA sequencers. These advances have enabled researchers to undertake large-scale sequencing projects that otherwise may not have been pursued. These include numerous projects underway to sequence entire genomes, including the human genome and various microbial, plant and animal genomes.

However, despite these advances in DNA sequencing technology, further improvements are required. Sequencing all of the DNA in a complex genome is a massive undertaking and, despite recent increases in throughput, requires up to hundreds of sequencers running in parallel for months or even years. In addition, the initial sequence of a genome typically contains errors, which then require additional sequencing to correct. To characterize the genetic diversity of an organism, researchers will need to sequence the genomes of many individuals and compare these sequences to identify differences. We also believe that researchers will want to sequence the genomes of more organisms as the cost of sequencing decreases. In summary, it is expected that the demand for DNA sequencing will continue to grow.

Genotyping is the process of analyzing locations within a genome where variations in a gene sequence, or genetic polymorphisms, are known to exist. Genetic polymorphisms play a role in an individual's susceptibility to disease and response to drugs. One type of polymorphism is a single nucleotide base variation, commonly referred to as a single nucleotide polymorphism, or SNP. Other types of variations involve changes in the length of simple repeating sequences and insertions or deletions of one or more bases at a particular location.

SNPs are the most common type of genetic variation. There are an estimated three to ten million SNPs in the human genome. While only a small fraction of human SNPs have been identified to date, we expect this number to increase dramatically during the next few years. For example, the SNP Consortium is a group of drug companies and public entities who are working together to discover 300,000 SNPs and contribute their findings to public databases. Numerous other individual companies have initiated programs to identify large numbers of human SNPs.

As more and more SNPs are identified, a new market is emerging for high throughput SNP genotyping. The simple identification of a SNP does not indicate whether or how it may relate to human health. To relate SNPs to disease or drug response, SNPs must be measured, or typed, in hundreds or thousands of people and correlated with clinical data describing the physical or mental health of those individuals. The emerging SNP genotyping market includes at least two segments:

Disease Association Studies. Disease association studies involve measuring specific sets of SNPs in healthy and diseased individuals to identify SNPs as markers for disease susceptibility and resistance. These studies could help researchers identify individuals who are at risk for such diseases as cardiovascular disease, hypertension, diabetes and cancer, and accelerate the discovery of new pharmaceuticals for these diseases. A single association study may involve typing up to 100,000 or more SNPs in thousands of individuals, requiring hundreds of millions of measurements.

Pharmacogenomics. Pharmacogenomics is the study of how individual genetic makeup influences drug response. The benefits of this knowledge include the potential for streamlining clinical trials by targeting a candidate drug to a specific responsive genotype, reducing both the cost and time of drug development. An additional benefit is the potential for tailoring drug prescriptions by genetic profile to maximize efficacy and minimize toxic side effects. Similar to disease association studies, a single clinical trial may require typing up to 100,000 or more SNPs in thousands of individuals.

Existing genotyping technologies do not provide the throughput, automation or economy needed for high throughput SNP analysis. Currently, the two leading techniques for SNP analysis are hybridization microarrays and enzyme detection methods.

Hybridization Microarrays. Hybridization microarrays are flat chips or glass slides which have different DNA fragments, or probes, located in known positions on the chip surface. Microarrays allow many SNPs to be measured at the same time on one DNA sample. This process of measuring multiple SNPs on one sample is called multiplexing. Researchers can only analyze one DNA sample on each microarray. Thus, microarrays offer a high degree of multiplexing but provide low sample throughput.

Enzyme Detection. Enzyme detection methods involve mixing a DNA sample with a specific enzyme and a DNA fragment of known sequence called a probe. There is one probe specific for each SNIP to be typed, and a signal generated during this reaction indicates the presence of a particular SNP. Researchers can perform these measurements in parallel using the current standard, microwell plates. Microwell plates are rectangular plastic plates which are roughly the size of a human hand and contain a number of small wells, each of which functions as a test tube. One advantage of this approach is that researchers can analyze different DNA samples in parallel on the same microwell plate. It is usually possible, however, to measure only a single SNP in each well. Thus, the overall throughput of enzyme methods is also relatively low.

Neither microarrays nor enzyme methods are ideal for high throughput SNP genotyping, where researchers need both high sample throughput and multiplexing capability, or the ability to measure multiple SNPs for each sample. New technologies are needed to meet the growing needs of this emerging market segment.

Gene expression analysis involves measuring the extent to which specific genes are expressed within a cell. A primary application of this process is differential gene expression analysis, where researchers compare the genes expressed in healthy and diseased samples to identify specific genes involved in a particular disease process. Another common application involves measuring a change in expression of certain genes when researchers add drug candidates to cells. As researchers identify more genes from the genome sequencing projects, the market for expression analysis technologies is expected to grow significantly.

The current leading technologies for gene expression analysis are the same as those previously described for genotyping. Researchers can use hybridization microarrays to monitor thousands of genes at the same time, but this approach is only feasible for relatively small numbers of samples, because only one DNA sample can be analyzed per individual microarray. Conversely, researchers can apply enzyme detection methods to large sample sets, but with that approach may measure only a single gene in each well of a microwell plate. It is submitted that neither of these approaches is suitable for measuring large numbers of genes over large numbers of DNA samples, as the testing of pharmaceutical drug candidates requires. A technology that could provide this capability would find rapid acceptance in the marketplace.

The genomics revolution is providing pharmaceutical researchers with a dramatic increase in the number of potential drug targets. A drug target is a molecule, usually a protein, which plays a role in a disease process and which researchers believe is a target for intervening in the disease process. In their search for new drugs, pharmaceutical researchers test many chemical compounds to determine whether they interact with drug targets. These researchers typically have large collections of chemical compounds to test against potential drug targets. In addition, in recent years pharmaceutical researchers have been vastly expanding the size of compound collections they use to screen against new drug targets. As a result, researchers require new laboratory technologies capable of screening increasingly large compound collections against an increasing number of drug targets in a cost-effective, automated and rapid manner. The market segments related to pharmaceutical drug screening are:

Assay Development. During the process of assay development, researchers develop methods for measuring the interaction of chemical compounds with specific drug targets.

Primary Screening. Primary screening involves testing entire compound collections against a drug target to identify "hits," or those compounds which exhibit activity against a drug target.

Secondary Screening. Secondary screening includes performing follow-up testing to validate hits identified in primary screening and further characterize their feasibility as a drug.

To screen a compound collection against a new drug target, a researcher must develop a test, or assay, for measuring whether particular chemical compounds in the library interact with the drug target in a certain manner. The type of assay selected depends on the drug target under investigation and the type of information being sought. Researchers design some assays to measure whether and how tightly a compound binds to a drug target, such as the binding of a drug to a protein. Other assays are designed to measure whether and to what degree a compound reduces the biological activity of a drug target, such as the activity of an enzyme. In other cases, researchers test compound collections against living cells and measure a particular cellular response, such as a change in expression level of one or more genes.

Current assay development methods are time consuming, taking from weeks to months, and are labor intensive, largely due to the need to measure a particular molecule within a mixture of many different components. In addition, current technologies for performing assays provide only a fraction of the information needed for selecting potential drug candidates. For example, existing technologies only allow researchers to measure a single gene at one time for the purposes of monitoring gene expression. Existing detection methods also typically require preparation of reagents in a highly purified form, which requires additional time and labor.

Primary screening involves performing an identical test on each compound in a large collection to identify hits. Based on the size of most compound collections today, primary screening can involve hundreds of thousands of individual measurements against a single drug target. The time, expense and labor required to conduct a primary screen currently limits the number of screens that pharmaceutical researchers perform, and thereby limits their opportunities for discovering new drugs.

A major element of cost in primary screening comes from the amount of chemical and biochemical reagents, including the drug target, required to perform large numbers of assays. The amount of reagents required is related to the total number of measurements and the volume of each measurement. Because of the high cost and the limited availability of many reagents, researchers have attempted to reduce the total consumption of reagents by reducing the volume of each measurement from hundreds of microliters down to three to five microliters. A microliter is one millionth of a liter. The success of these efforts, however, has been limited by the effects of evaporation on small sample volumes, the sensitivity of existing detection methods and the difficulty of delivering small volumes of reagents to microwell plates with speed and precision. For example, a volume of one microliter can evaporate from an open well in a few minutes, and even a small amount of evaporation reduces the reliability and precision of a measurement. Furthermore, the detection capability of many assay methods becomes less sensitive as the test volume is reduced. Researchers can improve sensitivity by increasing the concentration of reagents. This conflicts, however, with the objective of reducing reagent consumption. Due to these difficulties in reducing assay volumes, it is thought that researchers still perform most assays in primary screening in volumes ranging from tens to hundreds of microliters. A reduction in assay volumes would allow researchers to investigate more drug targets and perform primary screens using larger compound collections.

Secondary screening involves performing a variety of measurements on each hit identified in a primary screen. While the number of compounds under investigation is smaller than in primary screening, the number and diversity of measurements performed on each compound is much larger. The purpose of these measurements is to verify and further characterize the biological activity of each hit. For example, researchers may test each hit against the drug target at different concentrations to determine its potency. Also, each hit may be tested against multiple enzymes to identify activity against any of these enzymes. Current technologies typically measure only a single data point at a time, such as the activity of one compound on a particular enzyme, limiting the efficiency and economy of secondary screening, as well as the efficiency of overall pharmaceutical research.

In vitro diagnostic testing is the process of analyzing constituents of blood, urine and other bodily fluids. The two largest categories of in vitro diagnostic test performed today are general chemistry and immunodiagnostic testing. General chemistry testing utilizes relatively simple chemical reactions to measure certain molecules found in relatively high concentration in certain bodily fluids (usually blood). The most commonly performed tests include measurement of glucose, cholesterol and triglyceride levels. In contrast, immunodiagnostic tests involve complex biological reactions e.g., heterogeneous immunoassays, and test for molecules which are found in very low concentrations.

Chemistry and immunology-based testing of patient blood using automated analyzer equipment accounted for more than 60% of all IVD testing in 1994. Chemistry and immunology-based testing of patient blood using automated analyzer equipment accounted for greater than 60% of all revenue generated by IVD testing in 1994. IVD tests are performed predominately in hospital testing laboratories and commercial testing facilities using automated analyzer equipment. Unlike clinical chemistry analyzers, which perform mostly blood chemistry tests, immunology analyzers are used in various testing laboratories and perform antibody-based testing of a wide variety of analytes. Immunodiagnostic tests utilize the function of natural human protein molecules called antibodies. Antibodies have the ability to recognize and bind to specific analytes such as bacteria, viruses and metabolites. Existing immunodiagnostic testing typically involves sophisticated instrumentation and multistep protocols including sample dilution, variable incubation times and wash steps. Substantially all immunodiagnostic tests today are performed in centralized laboratories on complex instruments operated by skilled technicians.

As innovate and cost-effective technology becomes available, diagnostic testing is gradually migrating from high-volume clinical laboratories to point-of-care (POC) such as clinics, physician offices, homes, patient bedsides and emergency rooms. While clinical laboratories will continue to provide large volume testing, a new market is emerging for POC diagnostics which will provide for more frequent testing. POC testing eliminates the time and cost associated with utilizing remotely located laboratories, including those associated with specimen collection, preservation, transportation, processing and reporting of results. proprietary chemistry into microfluidic devices and sell value added products to R&D customers.

In addition to the existing companies that sell life science research products a new group of competitors has emerged that will also sell genomic-based products and these are generically termed biochip companies. Biochips encompasses a range of devices, some of which have little in common with semiconductor technology.

DNA chips are small flat surfaces on which strands of one-half of the DNA double-helix-called DNA probes or oligos are bound. Since one half of the DNA double-helix naturally bonds with its complementary other half-a process called hybridization-this type of chip can be used to identify the presence of particular genes in a biological sample. These chips, containing hundreds or thousands of unique DNA probes, are also called DNA microarrays and can be manufactured using a variety of techniques, including semiconductor processing technology, on a variety of surfaces, including glass and plastic.

The most common type of lab-on-a-chip uses microfluidics, a technique in which fluid samples move through tiny channels from one experimental site to another on the chip. The primary application for these devices is high-throughput screening, in which they are used to test biological samples more quickly at lower cost than conventional lab techniques.

Protein chips are similar to DNA chips except that they sample individual proteins that are coded for by the DNA. Sales of these devices is less than DNA chips because medical science is further from identifying and mapping all 100,000 to 150,000 proteins coded for by genomic DNA. The most significant and largest application for biochips is the use of DNA microarrays for expression profiling. In expression profiling, the chip is used to examine messenger RNA, which controls how different parts of the genes are turned on or off to create certain types of cells. If the gene is expressed one way, it may result in a normal muscle cell, for example. If it is expressed in another way, it may result in a turmor. By comparing these different expressions, researchers hope to discover ways to predict and perhaps prevent disease. Pharmacogenomics is a discipline that attempts to correlate a DNA pattern with the individual's response to drugs such as ability to metabolize a drug. The DNA pattern is obtained by studing single nucleotide polymorphisms (SNPs) that are found in all DNA. The clinical diagnostic applications of these technologies will follow and have major impact in cancer and genetic disease diagnosis although many believe that SNPs may be satisfactory to achieve patient profiling.

Single mode optical fibers have the unique feature of enhanced evanescent wave capability along with reduced mode cancellation that is seen with multimode waveguides. Previous work describes the use of tapered surfaces or fibers to conserve mode cancellation in multimode structures. The major problem with single mode systems is that the fiber or planar waveguides are very small in size as compared to a multimode waveguide system, making source and detector coupling very difficult. Multimode waveguides have typical sizes of 125 microns and larger, while single mode structures exist with typical sizes of 6 microns. The launching of light and overall manufacturing of system using single mode structures is difficult and expensive.

Total internal reflection ("TIR") fluorescence detection has been shown to provide enhanced sensitivity of fluorescent moieties close to or on the surface. See for example the work of D. Modlin described in WO 004364. This technique is often used to determine fluorescent events in chemistries where the fluid itself is opaque to the excitation or emission wavelengths of light being used. However, the Modlin device and approach has some serious disadvantages including the need for highly specialized plates and machinery where alignment is critical. It is also requires comparatively large volumes if sample and analyses and is not providing the commercially practical solution which are still sought. The use of evanescent waveguides for analyze sensing has been demonstrated in optical fibers by the work of Myron Block and Thomas Herschfeld References listed below). R. Sutherland, J. Herron, and M. Feldstein have demonstrated analyte sensing in planar waveguides. U.S. Pat. No. 5,961,924 by Reichert et al. describes enhanced sensitivity by utilizing a step gradient waveguide allowing for femtomolar analyte detection. Confocal microscopy detection is often used to interrogate fluorescent signals matrixed on microarrays however such devices are disadvantageously expensive thereby limiting their commercial practicality in the clinical laboratory setting.

A confocal scanning microscopy system needs to scan the array surface to determine analyte fluorescence. A confocal scanner, such as that available from GS1 Lumonics, Inc., is capable of low-level detection but requires a scanning of the micro-array surface, determining where each spot is defined and reducing fluorescent or scatter background. The microarray chemistry is spotted onto a solid surface by using one of several spotting techniques. A Cartesian Technologies spotter uses a series of pins to create individual spots.

The nature of the surface in which the spots are placed must be carefully known as the surface wetting characteristics will define the compactness of the spots on the array. If the spots are too close together on a highly wettable surface, cross-contamination occurs. Drop placement using the pin spotting is variable requiring the confocal microscopy scanner to always employ various algorithms to determine the spot locations. These requests of pre-scanning and precise location determination are preferably avoided.

Each micro-array system representing the current state of the art fails to adequately address the growing need for low-level detection, the control of individual micro-array spotted chemistries in a close packed density and a cost effective, manufacturable system.

References

Patent documents:

| | | |
|---|---|---|
| 5,402,514 | Booth et al. | Optical Waveguide Devices Including Day Photo Hardenable Layers |
| 5,961,924 | Reichert et al. | Integrated Optic Waveguide Immunosensor |
| 5,919,712 | Herron et al. | Apparatus and Methods for Multi-analyte Homogeneous Floro-immunoassays |
| 5,512,492 | Herron et al. | Waveguide Immunosensor with Coating Chemistry Providing Enhanced Sensitivity. |
| 5,785,874 | Eda | Optical Waveguide Device Bonded through Direct Bonding and a method for Fabricating the Same. |
| 5,814,565 | Reichert et al. | Integrated Optic Waveguide Immunosensor |
| 5,832,165 | Reichert et al. | Composite Waveguide for Solid Phase Binding Assays |
| 5,846,842 | Herron et al. | Waveguide Immunosensor with Coating Chemistry and Providing Enhanced Sensitivity |
| 5,959,292 | Duveneck et al. | Process for detecting Evanescently Excited Luminance |
| 5,907,408 | Naya et al. | Surface Plasmon Sensor |
| 5,677,196 | Herron et al. | Apparatus and Methods for Multi-analyte Homogeneous Fluoro-immunoassays. |
| WO 004364CI | D. Modlin | Evanescent Field Illumination Devices and Methods. |

Journal References

M. Feldstien et al., J. Biomedical Microdevices, 1:2, 139–153, 1999

T. Vo-Dinh, Anal. Chem, 71, 358–363, 1999

Micro-array technical Articles, Nature Genetics Supplement, Vol. 21, Jan. 1999

N. Witowski, "Technology Workshop on Genomic Micro-arrays," Mar. 21–22 2000

S. R. Quake and A. Sherer, "From Micro to Nano Fabrication With Loft Materials", Science, v. 290: 1536–40, year 2000

Text References

G. Boiside & A. Harmer, Chemical and Biochemical Sensing with optical Fibers and Waveguides, 1996, Artcch House, Inc., 0-306-46093-9.

SUMMARY OF THE INVENTION

The present invention addresses the above-identified need by providing a system and method for enhanced evanescent wave detection of bound biological molecules, individual spot configuration control and ease in manufacturing for use in diagnostic and related applications.

In particular, the present invention comprises an evanescent wave sensor having a single or multi mode waveguide and a number of micro-array spots, also called test wells, disposed in a cladding layer of the waveguide. Each of the micro-array test wells or other array configurations are preferably provided as an opening in the cladding layer or in a protected waveguide surface as more fully described later. Electromagnetic radiation propagating along The waveguide generates an evanescent wave (or evanescent field) extending to the test wells. The evanescent wave excites the fluorescently labeled molecules bound to the test wells, which excitation causes the fluorescent labels to emit a fluorescent signal. A detector located preferably below the waveguide senses the signal in the form of spherical radiation or anisotropic emission trapped inside the waveguide emitted by the fluorescent labels. The fluorescent radiation from one or more than one assay spots can be detected by using CCD type or other individual detectors. Alternatively, each test well can be sequentially scanned by having the excitation light address only one waveguide at a time corresponding to a single assay spot and the fluorescence collected by a single detector. Combinations of these approaches within a single device are also contemplated.

In the preferred embodiment of the present invention nano well micro-arrays are disposed in polymer waveguides in such a way that the target substances in the nano wells (for example, fluid samples, bound molecules) are within the range of the evanescent field generated by the electromagnetic radiation propagating in the waveguide. For example, the nano wells can be located inside the cladding layer of the waveguide, or in an intermediate cladding or in other waveguide protective layers, as long as the wells are within the range of the evanescent field. The present invention contemplates that the bound molecules in all the wells in the array can be exited by the evanescent field of a common waveguide. It is also contemplated that an individual test well or a limited number of test wells can be subjected to the evanescent field of an individual waveguide. The presence of the target substances in fluid samples conveyed to the nanowells by way of microfluidics is sensed by using the evanescent field to excite the fluorescent labels of the target substances and detecting the emitted fluorescent radiation by PMTs or a CCD located on the opposing side of the waveguide relative to the nano well array.

The waveguide of the present invention is preferably made of Polyguide, described in U.S. Pat. No. 5,402,514 the teachings of which are fully incorporated herein by reference. The waveguide system for biosensors comprises microwells, preferably as an array, which are formed in a cladding layer and disposed at such positions that the samples contained in the wells can be affected by the waveguide's evanescent field. The waveguide may optionally have an additional cladding material at the side opposite to the array. When an electromagnetic wave propagates along the waveguide, the difference between the refractive indices of the waveguide's core and the cladding layer leads to the creation of an evanescent field in the cladding layer (or a layer adjacent to the waveguide's core). The presence or absence of the bound materials in the microwells can alter the characteristics of the evanescent wave and these altered characteristics may be detected either within the light wave propagated within the waveguide, or more preferably, at directions generally orthogonal to the plane of the waveguide. In a most preferred embodiment, a fluorescent label associated with a target substance of a fluid sample in the microwell is excited by the evanescent wave either directly or via a capillary pathway, causing the label to fluoresce. The emitted fluorescence may be conveniently detected by a suitable photomultiplier tube (PMT) or CCD detectors, which are mounted opposite to the array to avoid the need to measure the fluorescence through the fluid sample. Other molecule classes can also be excited by evanescent energy including proteins, nucleic acids, steroids and other molecules with closed ring structures with appended substitutions or additions to the rings.

The waveguides of the present invention permit the creation of disposable molecular diagnostic devices having photonic excitation integrated within the device. Additional polymer layers can be optionally added to the surface of the waveguide, permitting creation of microfluidics. The resulting devices can comprise photonic waveguides, fluid channels, valves drains, reflux chambers, reservoirs, and minicolumns on top of the microfluidic entry portal that will permit micro to nanoscale sample preparation prior to detection. Advantageous aspects of various embodiments of the present invention include:

1. embedded single or multimode waveguides for evanescent excitation of labels such as fluorophores, thereby providing the first fully integrated chemistry platform from sample prep to signal generation;
2. integrated fluidic channels that permit heterogeneous molecular diagnostics;
3. automated "printing press" photolithography can be used to create the planar waveguides; all manufacturing steps can be automated;
4. custom polymer linkage groups built into the waveguide material or into thin waveguide protective layers to optimize attachment of desired capture molecules such as DNA, protein (antibodies), RNA (aptamers), RNA (aptazymes), etc.;
5. customize polymer composition to accommodate most wavelengths of light required to excite selected fluorescent labels;
6. ability to configure in any size including film strips analogous to 8 mm, 16 mm or 32 mm film (e.g., any commercially convenient sizes and for sake of simplicity only 8 mm will be referred to hereafter although all sizes are contemplated thereby) thus providing the ability to analyze 100,000s to millions of oligo probes simultaneously using a single DNA sample such as a single patient's DNA e.g., SNP pattern;
7. flexible waveguide film format allows thin film chemistry technology including ability to distribute small fluid volumes evenly along a long strip of film;
8. nanowells prepared in the cladding layer serve as reaction chambers that optimize chemistry thermodynamics and minimize sample to sample cross talk; polymer wetablity easily achieved using plasma discharge technology;
9. the powerful evanescent tail excitation permits the creation of a sensitive fluorescent label detection platform;
10. light polarization can be employed for detection purposes; and
11. different light wavelengths may be employed for different purposes, such as long wavelengths for heating cycles.

The current invention is capable of addressing applications involving genomics, RNA and DNA analysis, pharmaceutical drug screening and clinical diagnostic testing in addition to the pharmaceutical drug screening market as well as applications across other industries, including chemical processing, environmental and food testing and clinical diagnostics.

A significant advantage of detecting bound fluorescent molecules that are excited using an evanescent wave is that the emitted fluorescent light can be detected outside the aqueous reaction solution. Most complex biological solutions contain molecules that quench fluorescent emission. This means that when a fluorescent molecule is excited it emits a photon and rather than being detected as a signal of a specific binding reaction, the photon is often captured or absorbed by surrounding biological debris or material in the aqueous suspension which are located between the point of emission and the detector. This absorption is often referred to as quenching and has been associated with conventional assay configurations that emit photons to go through a complex biological matrix prior to detection. Positioning the detector at the opposite side of the avoids the disadvantages of the conventional quenching phenomenon.

Another aspect of the present invention is to provide a device which allows the growth of tissue culture cells on the surface of waveguides and then to monitor intracellular binding reactions with or around such cells without killing and staining the cells. Ultimately this may be required in many cell-based disciplines including virology or proteomics which seeks to discover what newly discovered proteins do once they are inside cells or bound to the cytoplasmic membrane or other intracellular organelles. A unique property of tissue culture cells bound to a solid surface is that they conveniently "flatten out" and therefore their internal organelles, nucleus, endoplasmic reticulum, ribosomes, etc. are very close to the surface of the solid surface to which the cell is attached to. Fluorescent probes (proteins, peptides) which enter the cell and bind to targets can be advantageously detected the same way other binding reactions are detected with the evanescent detection system—only bound material close to the surface is measured.

Another advantageous aspect of the present invention is the ability to monitor chemical sensing reactions in "real time". The chemistry is advantageously added to the top of a waveguide device and the binding is read from the bottom while the reaction is occurring. As a result, the rates of reactions can be directly measured and this permits determination of the extent of binding and association and disassociation rates. Furthermore, binding reactions can be stopped when they reach completion or saturation.

BRIEF DESCRIPTION OF THE DRAWINGS

Further understanding of the current invention may be had by reference to the figures wherein.

DETAILED DESCRIPTION AND BEST MODE

Light rays propagate or travel inside a thin film (waveguide having refractive index $n_1$) according to the principles of total internal reflection of light, if the waveguide is optically denser than the medium surrounding the waveguide (plastic or other material forming a cladding layer with refractive index $n_2$). Therefore for $n_1 > n_2$ and certain angler of incidence the light rays do not refract into the medium surrounding the waveguide, but totally internally reflect into the waveguide at the interface between the waveguide and the medium. As follows from Snell's law, $$n_1 \cdot \sin \Theta_1 = n_2 \cdot \sin \Theta_t$$

where $\Theta_1$ is the incident angle of light on the interface, $\Theta_t$ is the angle of refraction.

For the critical angle $\Theta_c$, $n_1 \cdot \sin \Theta_c = n_2$, and $\sin \Theta_c = n_2/n_1$. For the angles of incidence greater than the critical angle, the light is totally reflected at the interface. As a result of this phenomenon, light rays propagate in the optical guides by multiple total internal reflections.

If the cladding layer with a refractive index $n_2$ is thought of as the walls of a tunnel, then the light rays are confined within the tunnel if their launch within the tunnel is equal or greater than the required TIR angle because the refractive index of the cladding material or walls $n_2$ is lower than the refractive index of the waveguide tunnel material $n_1$.

If the thickness of a thin film waveguide is 4–6 microns, then the light in the waveguide is predominantly single mode, which means that light rays travel through the waveguide in parallel without destructive or constructive interference between the light rays. Although the light reflects back into the waveguide at the conditions described above, single mode waveguides produce an evanescent field, which is an electromagnetic field extending beyond the interface and attenuating in the second medium. The evanescent wave is a photonic light effect that is created due to the phenomenon of frustrated total internal reflection between two closely spaced or contacted media. When an electromagnetic wave travels along an optical conductor which is in contact with a second medium having a lower index of refraction, the electromagnetic wave undergoes a total internal reflection at the interface between the optical conductor and the second medium. For certain phase differences between the incoming and totally reflected waves electromagnetic field, which is called the evanescent field, reaches beyond the interface and is present in the second medium. For thin film waveguides of the type described above, the evanescent field can extend more than 6 microns above the interface, depending on the medium surrounding the plastic waveguide material. Air and water reduce the reach of the evanescent field beyond the interface, because their refractive indices are low compared to such cladding as cellulose acetate bityate (CAB).

The evanescent field extends beyond the interface between the waveguide and the cladding layer to varying distances depending on the composition of the cladding layer. It is possible to lay more than one cladding layer on top of the waveguide layer. We discovered that a thin first cladding layer of up to 6 microns can be deposited on top of the waveguide and at least one additional cladding layer can be deposited on top of the first cladding layer, while the two layers remain within the reach of the evanescent field.

As will be described in more detail below, the first cladding layer protects the waveguide layer from undesirable foreign material or particles, which is needed to reduce scattering of light on the surface of the waveguide and therefore reduce possible sources of noise or spurious signals. Additionally, the first cladding layer deposited on top of the waveguide can be made from material containing chemical binding groups designed to bind desired molecules such as protein, DNA, RNA, lipids, carbohydrates, etc. Such a cladding layer might be as simple as a coating of a polymer or even a molecular layer applied by vapor deposition and having the desired properties. We have discovered that the evanescent wave will sweep across and above this protective cladding layer depending on the incident angle of the source light into the waveguide, the thickness of the protective layer. Of course, the first cladding layer must have a refractive index lower than that of the waveguide material. An advantage of such evanescent field is that it can excite those fluorescent molecules which are bound to the surface of the waveguide in specific complexes such as DNA-DNA hybridization, antigen-antibody, aptamer-protein, etc. Free fluorophores not bound to specific targets in the solution float above the reach of the evanescent field and thus generally are not excited by that field. The excited fluorescent labels emit light that may be detected using PMT or CCD technology.

Figure 1:
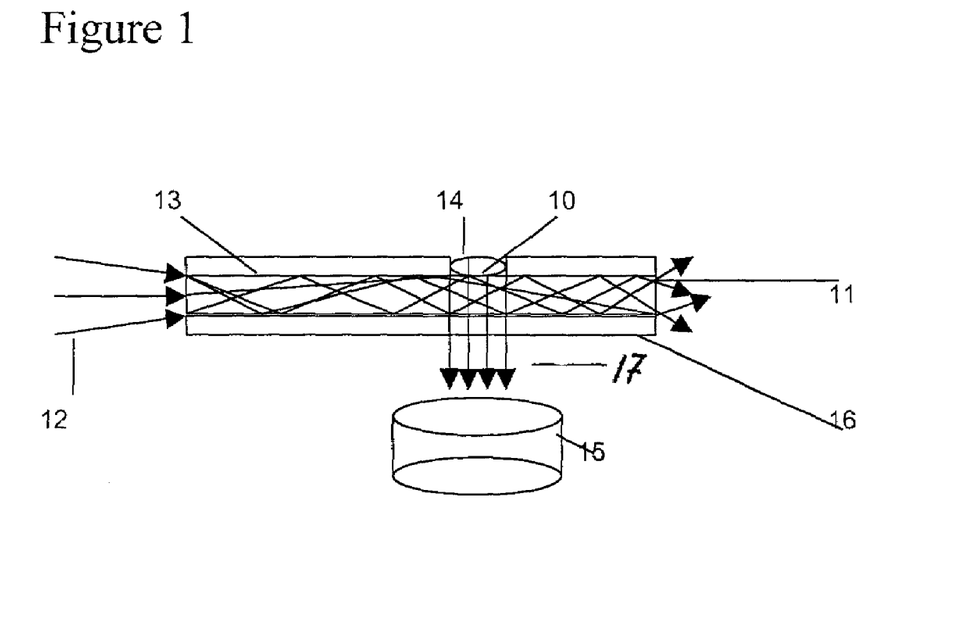
FIG. 1 shows a cross-sectional view of a preferred embodiment of the present invention.

The instant invention advantageously employs an integrated detection system comprising a polymer waveguide that creates an evanescent wave capable of exciting fluorescent molecules (or other molecules) bound to the surface of the waveguide or the surface of a protective layer (described at greater length later) within one or more microwells. Turning now to FIG. 1, a schematic representation of a detection device of the present invention comprises a waveguide film 11 sandwiched between a first cladding layer 13 and a second cladding layer 16. First cladding layer 13 has at least one test well 14 of a size determined by a particular application. As an example, the diameter of test well 14 can range from as small as a few microns up to 25 microns for analyzing DNA-DNA hybridization, antibody-antigen binding, aptamer-protein binding, etc. As can be seen in FIG. 1, an aqueous sample 10 is placed into test well 14, meaning that any chemical reaction taking place in sample 10 occurs in a close proximity to waveguide film 11. Since the refractive index of waveguide film 11 is greater than that of first cladding layer 13 or sample 10, single mode or multi mode electromagnetic radiation 12 propagating along waveguide film 11 will totally internally reflect from the interface between the waveguide film, creating an evanescent field reaching at least a portion of sample 10. The portion of sample 10 affected by the evanescent field is usually disposed closer to the bottom of test well 14, therefore, closer to waveguide film 14. If certain target substances in sample 10 reached by the evanescent field are labeled with fluorescent molecules capable of being excited by the evanescent field, the excited labels emit fluorescent radiation 17 which can be detected by a detector 15. Detector 15 can be, for example, a PMT or a CCD detector. The intensity of the emitted fluorescent radiation 17 is proportional to the concentration of the fluorescent labels present in sample 10. In many practical applications the evanescent field will excite the fluorescent labels bound only to a particular type of molecules present in sample 10, therefore making it possible to detect and measure the concentration of that particular type of molecules.

Depositing a second cladding layer on the protective cladding layer makes it possible to provide holes or other passage ways for liquid communication with, and thus access to, the protective cladding layer. The thickness of the second cladding layer determines the dimension of the hole, which becomes a reaction chamber or 'nanowell'. The dimension of a nanowell defines the volume of a fluid contained in it, which is preferably from 1.0 pLiter up to 1.0 nLiter, or any other volume determined by the thickness and diameter of the nanowell. An important aspect of this invention is there can be several claddings, limited only by the net thickness and the refractive index of the layers. What matters is that the evanescent wave be capable of exciting bound fluorophores or other molecules. If it does not, then it means that a different configuration and/or choices of materials of the cladding layers with different refractive indices, as well as different incident angles $\Theta_1$ should be selected.

The invention according to FIG. 1 uses single or multimode polymer waveguides 11 that produce an enhanced evanescent field for exciting bound assay components that are associated with micro-array spots. In one embodiment (shown in FIG. 1) the waveguide 11 is sandwiched between a first cladding layer 13 and a second cladding layer 16, where the first cladding layer 13 comprises test wells 14 in which test sample 10 contacts waveguide 11. The interface between the waveguide 11 and cladding layer 13 is ideally treated to provide for a wetted chemically activated surface for the binding assay before depositing first cladding layer 13. The described surface treatment allows for uniform spotting in a very controlled closely packed configuration, while minimizing analyte cross talk between spots using this micro-well configuration. The wells can also be deeply configured so that individual micron columns can be used above each spot In another embodiment, an intermediate cladding or protective layer (not shown) is placed between waveguide 11 and first cladding layer 13. This protective layer can serve to shield the waveguide 11 from chemical or other destructive effects of sample 10 to be tested. In addition, this protective layer may be advantageously modified chemically as necessary to provide binding sites for analysis components (e.g., DNA, antibodies, etc.) using chemical attachment techniques well known in the art. Laying a protective layer represents a significant departure from conventional approaches of direct waveguide coupling and is made possible by the proper selection of materials, their thickness, and incident angles. The evanescent field can be made to sweep through and above the protective layer. The reach of the evanescent field will be a function of the refractive index and thickness of the protective layer, which are adjusted so that the evanescent field extends sufficiently into the test well to excite bound molecules or the molecules closest to the surface of the waveguide. In an ideal construction, this protective layer will be combined with microfluidics for proper sample handling.

Figure 2:
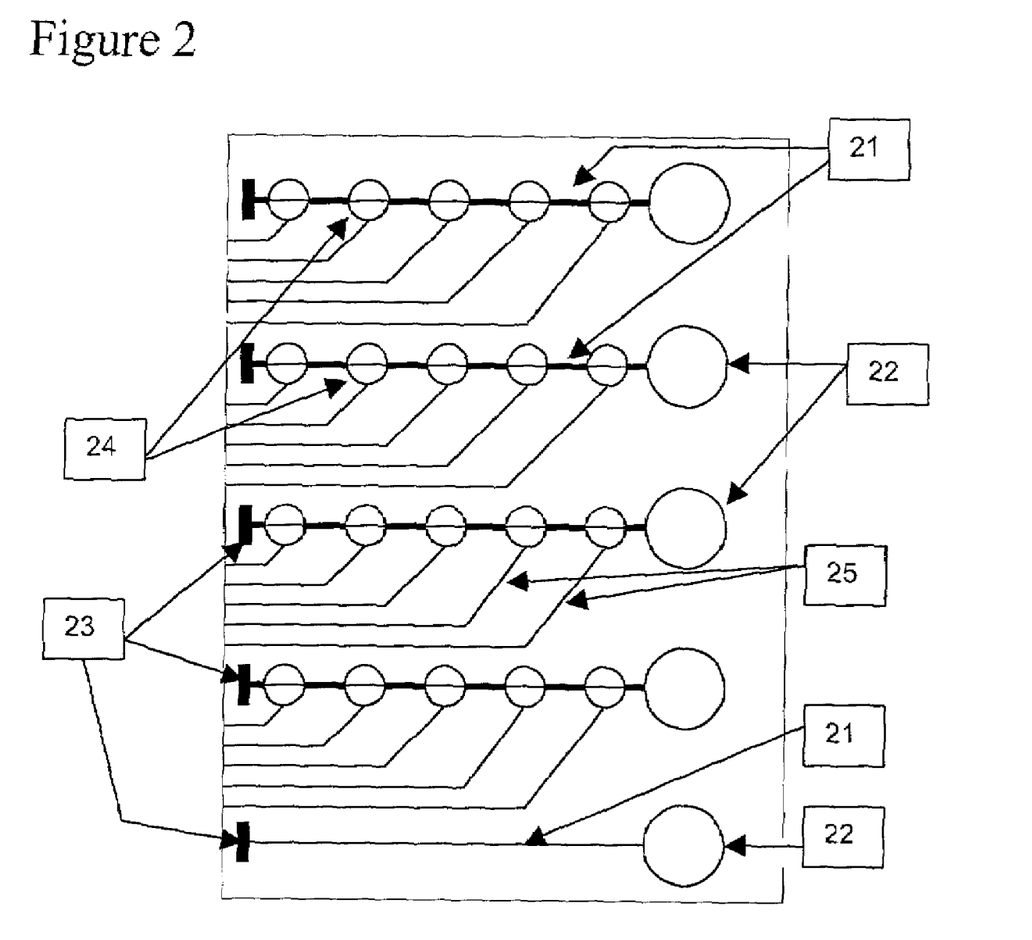
FIG. 2 shows a top view of an array of microwells with associated waveguides and sample directing capillary channels.

With reference to FIG. 2, the microfluidic array films shown on that Figure comprise multiple fluidic networks or capillary channels 21 with sample wells 22, capillary vents 23 and reaction wells 24 arranged in a grid or array format. Each fluidic network 21 performs a measurement on a different sample simultaneously, but through separate waveguide excitation channel 25. This capability, known as parallel processing, provides two major advantages. The first advantage is the higher sample throughput, which results from performing measurements on many samples at the same time. The higher throughput provided by the instant films will be a significant benefit in applications such as DNA sequencing and SNP detection. The second advantage is that each measurement is performed in a separate fluidic network 21, thereby avoiding the potential for cross-contamination of different reactions on the same film. The micro-array configuration illustrated in FIG. 2 can be seen as a micron-titre plate comprising wells as small as 6 microns deep.

In many applications, the instant polymer waveguides with suitable reagents enable researchers to perform high content measurements, allowing them to obtain more information from each measurement than is currently possible with microwell plates. For example, many different SNPs or genes can be detected in a single reaction, whereas microwell plates typically allow the detection of only a single SNP or gene in each reaction. The microfluidic array films of the instant invention integrate these high content measurements with parallel processing, thereby providing an enhanced combination of high throughput and multiplexing in applications such as gene expression analysis and SNP detection.

The polymer waveguide devices of the type disclosed in this description also allow researchers to perform most measurements faster than with conventional instrument systems. For example, it is estimated that the sequence of a DNA strand can be determined in less than 20 minutes using the waveguide device. A similar experiment often requires over two hours on a capillary array DNA sequencer. In some applications, the devices of the current invention will allow researchers to perform measurements 100 times faster than with conventional systems. A mixture of DNA fragments in a genotyping application can be separated in less than one minute, for example, compared to two hours on a conventional instrument.

Most laboratory analyses involve a number of instruments and require the movement of fluids and reaction components from one instrument to the next. The integrated fluidic circuitry of the devices of the instant invention allows researchers to perform multiple experimental operations in sequence on a multiplex array. The fluidic microchanneling illustrated in FIG. 2. is advantageously comprised of interconnected microchannels, through which fluids and other materials are pumped, monitored and controlled by computer. By reducing the number of human intervention points, the inventive devices reduce the potential for variability and error and increase the data quality. For example, microfluidic films for miniaturization and integration of the multiple sample preparation steps required prior to DNA sequencing can be designed using the techniques of the instant invention. Because the inventive devices perform measurements on very small volumes of material, smaller amounts of sample and reagents are consumed. For example, the preferred devices of the instant invention allow measurements in as small as one-thousandth of the volume typically used in a microwell plate.

A primary reason why prior efforts at deploying this technology have failed is because glass waveguides which are brittle, too difficult to manufacture consistently in high volume and consequently too expensive or upon molded and embossed polymer waveguides have also suffered from inconsistency due to mold deterioration and imperfections which arise during the molding process. The instant invention takes advantage of the polymer waveguides that can be created using the Polyguide material made by Dupont. Waveguides in this material can be created using a diffusable polymer which can then be "activated" using UV. By masking the polymer and controlling the areas irradiated by the UV, the waveguides can be created with exquisite dimensional control allowing creation of near perfect waveguides at the rate of 1000s of waveguides per hour.

Referring to FIG. 4, a waveguide of the instant invention comprises a polymer film 41 produced by extrusion. The waveguide is preferably formed using Polyguide, a material available from Dupont, that utilizes monomer migration to create a varying index of refraction in the polymer. The process is disclosed in U.S. Pat. No. 5,402,514, the teachings of which are incorporated herein by reference, and illustrated in FIGS. 4a–4f. However, other alternative materials are also contemplated including for example polycarbonate. For ease of discussion reference shall be made to Polyguide, however, it will be understood that the invention is not to be construed as being limited to this material. As shown in FIG. 4a, masking 42 and subsequent exposure of Polyguide to UV light 43 lead to the formation of the waveguide structures that can be used for evanescent wave biosensors. Based on the thickness of polymer film 41, these waveguides can be either multimode or single mode systems.

Figure 4A:
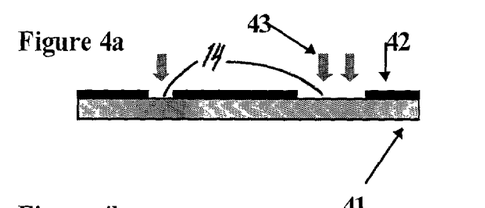
FIG. 4 shows a preferred manufacturing process for making polymer waveguides.
Figure 4B:
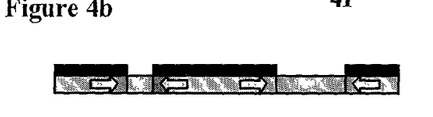
Figure 4C:
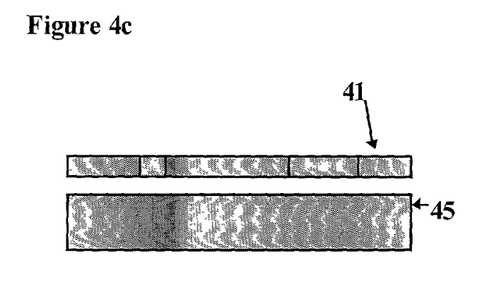
Figure 4D:
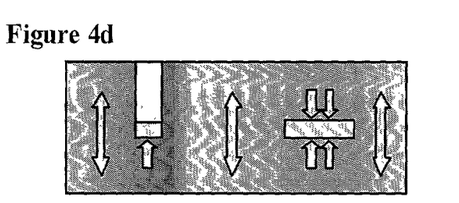
Figure 4E:
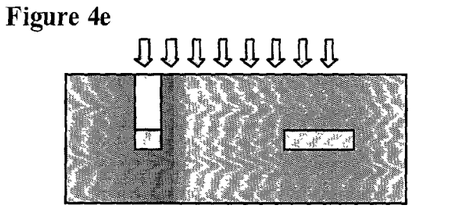
Figure 4F:
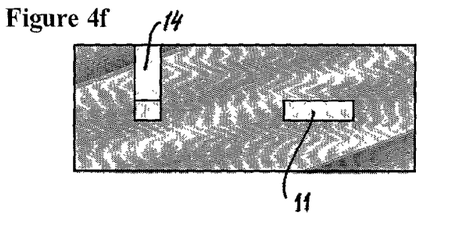

In one embodiment, portions of the cladding layer are burnt off (depleted) by the UV light, forming test wells 14, so that when sample 10 (shown in FIG. 1) is deposited in test wells 14, the sample contacts polymer film 41. Alternatively, if there is a protective cladding layer or coating (deposited by spray or chemical vapor deposition, etc.), such protective layer shields the waveguide material from the test liquids of sample 10. Additionally, such a protective layer could provide chemical binding means to permit attachment of antibodies, proteins, nucleic acids or other components of a diagnostic assay system to the waveguide layer. Constituents in the fluid are then bound to the surface of the waveguide (or the protective layer) using many of the available binding chemistries, such as covalent bonds, antibody/antigen reaction and hybridization. The thickness of the protective layer, its optical refractive index, and the incident angle of the light in the waveguide are all advantageously optimized to control the dimensions of the evanescent wave extending beyond the protective layer. FIG. 4b shows the primary diffusion process (depicted by arrows) following exposure to the UV light in FIG. 4a. Thereafter, a bottom cladding layer 45 is ideally laminated onto the waveguide 41, as shown in FIG. 4c. Secondary diffusion process is shown in FIG. 4d, after which the waveguide material is photoexposed, as shown in FIG. 4. to cause cross-linking and finalize the formation of waveguide 11 and test well 14, as shown in FIG. 4f.

Figure 5:
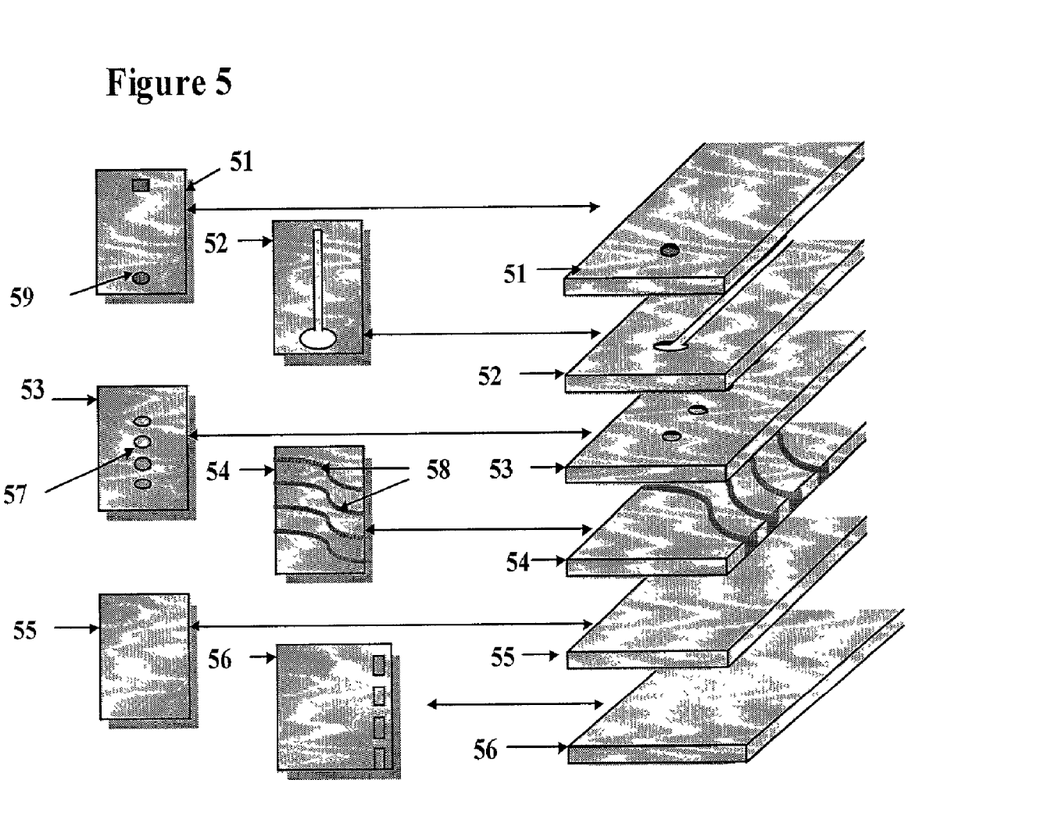
FIG. 5 shows a perspective view of the construction of a preferred polymer waveguide device.

With reference to FIG. 5, an embodiment of a biosensor of the present invention preferably comprises a number of layers, including a top layer 51 having a port 59. Top layer 51 is disposed above a fluidics layer 52, which in turn is disposed above a first cladding layer 53. An air vent system (not shown) helps to fill various capillaries in fluidics layer 52 and micro cuvettes shown in first cladding layer 53 with a sample fluid. First cladding layer 53 comprises one or more micro cuvettes 57. A layer 54 disposed under first cladding layer 53 may either be the waveguide itself, as shown, or a thin protective layer bound to the waveguide. Layer 54 would be the one that exhibits wetting characteristics, so that when the sample fluid is deposited into port 59, the sample fluid would rapidly flow onto the surface of layer 54 rather than "bead-up." First cladding layer 53 masks the wetted surface of layer 54 everywhere except for the locations of micro cuvettes 57. For micro-array geometries where pin spotters are used, the spotting pin placement tolerance is not as critical as applications where a micro cuvette is not used. The thickness of layer 53 is in the order of 6 microns, but can be much thicker. A second cladding layer 55 is disposed at the opposite side of layer 54 above a supporting layer 56. Layer 54 comprises waveguides 58 capable of conducting light. During the operation of the biosensor shown in FIG. 5, either a single or multiple waveguides 58 can be used to propagate light in the biosensor. If supporting layer is not transparent to the fluorescent light, that layer would need to have a hole or series of holes allowing the fluorescent light generated by the excited fluorescent labels of the biological molecules to pass through the holes and be detected outside the supporting layer. In layer 54, excitation light can be focused into a single waveguide 58 individually or a plurality of waveguides 58 simultaneously. The excitation light is focused into the edge of the waveguide film addressing each of the waveguides. If a single detector is used to detect the fluorescent light from each waveguide 58, then a photomultiplier tube (PMT) could be used to provide very sensitive fluorescence detection. If all the waveguides are illuminated at the same time, then a charged coupled device (CCD) detector should be preferably used.

Supporting layer 56 can be a continuous tape or 16/35 mm film configuration. The continuous film configuration would lend itself to array geometries sized so they are easy to work with yet offer tens of thousands of spots for Genomics. This system can be ideally configured with single or multimode guides in either single or multiple reading systems. The preferred waveguide material from DuPont, Polyguide, utilizes monomer migration to create plastic sheets with varying indices of refraction. The light masking of the Polyguide material allows for the creation of very fine waveguide structures that provide a cost-effective way to form various array detection schemes. Each of the waveguide structures can be designed to have unique binding chemistries immobilized on their open surfaces to create a multiple assay platform.

The coupling of fluorescence source energy into a single mode planar waveguide can be accomplished by providing a mirror cut at one end of the waveguide. Light either below or above the waveguide would then be reflected into the waveguide. If sequencing of light is required, it would then be necessary to move the waveguide or source to provide sequencing of the individual waveguide mirrors. It should be mentioned that grating couplers and unique v-notch couplers can also be used to provide coupling to waveguides. In the case of a v-notch coupler the light is brought onto the waveguide, and bubble switches can be used if sequencing of light is required. Again, the sequencing is employed if a single detector is used. Multiple detectors such as CCD arrays do not require sequencing.

The use of a single mode planar waveguide is preferred, since it provides a strong evanescence field useful for excitation of fluorescent labels. If Ru, Eu or other similar well known fluorescent labels are used, the naturally occurring fluorescence in materials or the sample can be advantageously gated out of the detection system. The Ru or equivalent fluorescent labels providing large stoke shifts and time resolved or phase modulated fluorescence can be utilized. However, multi-mode waveguides, while creating a weaker evanescent field, permit to launch more light into the waveguides and, depending upon the physical characteristics of the particular system used, are preferred.

The evanescent wave in the present sensor is very powerful—all bound fluorophores become excited, therefore making the evanescent excitation a very efficient means of exciting fluorescent molecules. Despite these advantages, past attempts have commercially failed to harness the evanescent wave for primarily two reasons. All previously available materials e.g., glass, sapphire, molded plastic, etc. proved to be either too expensive or inconsistent i.e., not manufacturable. In addition, a suitable means for producing microarrays of nanowells in combination with useful waveguides was absent.

The waveguides are advantageously embedded into the polymer by photolithography. Cladding layers 42, 43 and fluidic layers (52, FIG. 5) are preferably added during production. Physical processes are used to move liquids through interconnected channels within the multilayered device. Since fluids are contained within the device, they are less prone to evaporation. With additional reference to FIGS. 2 and 5, the microfluidics technology of the instant invention enables accurate measuring, dispensing and mixing of volumes many times smaller than what researchers commonly use. In this manner, a variety of fluids can be precisely manipulated, including those that contain whole cells, cell fragments or magnetizable particles, using computerized controls. As a result, the devices of the instant invention can be used to perform large, complicated experiments faster and with greater accuracy than with existing conventional systems, and at a reduced cost. Additional understanding of microfluidics is provided in S. R. Quake and A. Sherer, "From Micro to Nano Fabrication With Loft Materials", Science, v. 290: 1536–40, year 2000, fully incorporated herein by reference. Another advantage of the present invention is the use of flexible waveguides since flexible polymer materials offer advantages over non-flexible or rigid materials for fluid handling and movement. This represents a significant advantage over conventional approaches which have relied upon inflexible waveguide materials.

Figure 3:
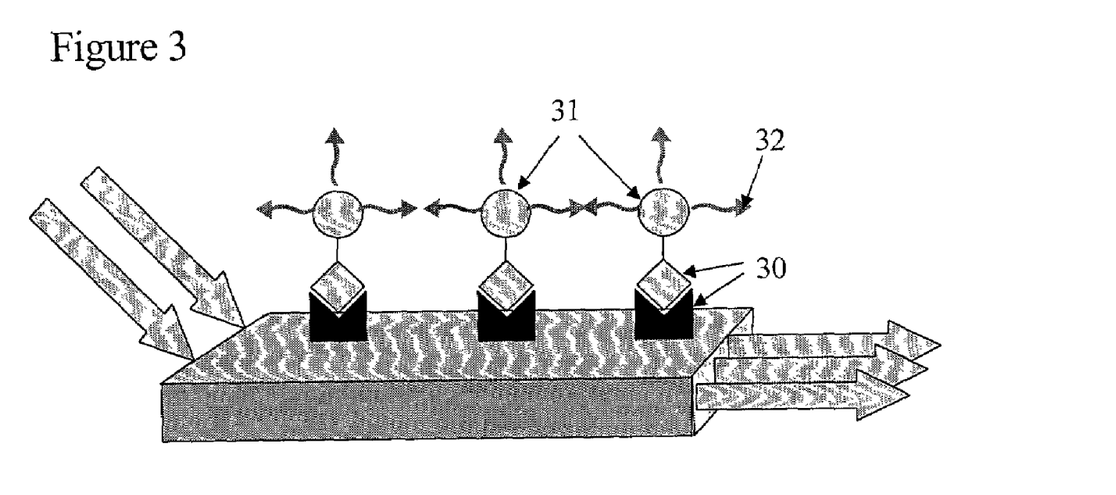
FIG. 3 shows a perspective view of a biophotonic sensor.

The power of the multilayered microfluidic films of the present invention can be enhanced by using the reagents capable of detecting the presence of a member of a binding pair in a test sample. For example, the test may employ an immobilized antibody for detecting a specific antigen in the sample. Additionally, a fluorescently labeled antibody specific for another epitope on the antigen may be included within a test reagent. Referring to FIG. 3, for example, a Biosensor of the present invention is typically a device comprising a biological component 30 having a fluorescent label 31, component 30 being coupled to a waveguide surface, as shown in FIG. 3. Fluorescent labels 31, when excited, emit a fluorescent signal 32 for detection and analysis. These chemicals are added to a sample to perform a measurement, which in this example would be a conventional immunoassay sandwich assay. Many other such immunoassay detection techniques may be modified to take advantage of the instant invention. For high throughput applications, the instant devices may be complemented with multiple networks of microchannels in order to analyze many samples in parallel as discussed later in greater detail.

Also contemplated by the present invention is a cassette concept analogous to a 8 mm film in a cassette. Hundreds of thousands or millions of DNA oligos e.g., representing 300,000 SNP sequences, can be advantageously printed onto strips of the polymer waveguide or polyguide film and loaded into disposable cassettes. In use, a sample of DNA is then loaded into the cassette which will also ideally contain all necessary reagents and washes. A reader comprising a photomultiplier tube (PMT) or charge coupled device (CCD) will read the photonic array and the resulting digital pattern used for patient prognosis and diagnosis.

The waveguide films of the present invention are also capable of analyzing many samples simultaneously, which is commonly referred to as parallel processing.

The waveguide polymer films may be readily produced by extrusion or other methods and optionally can be mounted on virtually any support including glass when desirable. The instant invention can ideally offer advantages over silicon and glass chips in most applications including for example, the capacity to be made over a broader range of functionality, size, thickness and format than is believed possible with glass or silicon chips. This design flexibility provides significant latitude in developing films for different applications and performance levels. In addition, the polymer films can be manufactured at a significantly lower cost than possible with glass chips. The instant devices can ideally be used as single-use disposables in most applications. Thus, there is no possibility of carryover of sample fluids or reagents from one measurement to the next. Which is a significant advantage over multi-use glass chips in applications, such as pharmaceutical drug screening.

EXAMPLE

Prototype chemical sensor waveguide devices were created by bonding a glass fiber optic wire to a flat polymer waveguide. The flat polymer material used for the waveguide is described in Table 1 of U.S. Pat. No. 5,402,514 fully incorporated herein by reference. A fiber optic wire was disposed in such a way that emitted light would be coupled or launched into the waveguide and travel through the waveguide generally parallel to the surface of the waveguide. The other end of the fiber optic wire was attached to a helium-neon laser light source. Therefore, the light was transmitted through the fiber optic wire and entered the polymer waveguide. Red light from the helium-Ne laser was visible inside the waveguide. A cladding layer of cellulose acetate butyrate ("CAB") with a refractive index lower than that of the polymer waveguide material was bound to liquid polyguide material at one side of the waveguide. A cladding layer of CAB was bound to the other side of the flat polymer waveguide. However, a portion of the waveguide from a defined region on top (an arbitrarily chosen side) was not clad with CAB and was designed to serve as the chemical-sensing region in which a sample fluid could contact the surface of the exposed waveguide and be detected.

Additional prototype devices had layers of CAB of different thicknesses. The devices were constructed with a CAB cladding layer having a thickness of 6 microns (0.006 millimeters) and some had 12 microns, 18 microns, 24 microns, 30 microns and 50 microns. A small volume (1–3 micrometers) of a fluorescent dye in solution (cy5) (available commercially from Molecular Prodes Oregon) was placed on top of the exposed waveguide where there was no cladding. This was a positive control sample. A small volume of water (1–3 microliters) was placed next to the fluorescent dye. This served as a negative control sample. When light was launched into the waveguide device the fluorescent spot was clearly visible while the water spot was not visible. During the application of the fluorescent dye a small amount (a drop) accidentally fell onto the 6 micron thick cladding material away from the positive and negative controls but above the illuminated waveguide. Surprisingly, the fluorescent material emitted light. Water placed on the cladding material above the light and next to the fluorescent material did not emit light. Evidently, the evanescent field was able to reach above 6 microns of the cladding material, although it was expected that the cladding layer would reduce the evanescent field.

We then placed positive and negative control samples on top of waveguides having cladding layers of 6, 12, 18, 24 and 30 microns in thickness. Fluorescent dye in positive control samples emitted light on all the waveguides tested. We then tested a waveguide with a 50-micron thick cladding layer. No light was detected, which indicated that the evanescent wave could not penetrate through the 50 micron cladding layer. Therefore, it is now possible to create sensing devices with multiple layers of cladding material above the waveguide material. One advantage provided by such devices is that unique materials, such as chemically defined polymers with reactive groups specific for desired capture ligands, can be deposited on to the waveguide layer as a first cladding layer and then another layer with holes or channels or wells can be added, creating a novel chemical sensing device. A major advantage is that the thickness of the first cladding layer (or protective layer) can be designed to achieve optimal excitation of molecules bound to its surface (as opposed to the free molecules not bound to the surface). The first cladding layer can also advantageously protect the integrity of the waveguide material from any adverse reaction with the aqeous material under tests.

Furthermore, when light is launched into the waveguide at an angle greater than the critical angle, the height of the evanescent wave or distance it can penetrate above the surface of the waveguide changes. For incident angles smaller than the critical angle the propagation is lost as the light refracts into the cladding layer and escapes the waveguide.

Various devices were created to perform chemical binding experiments on the surface of waveguides. It was discovered that substances placed on top of the waveguide with a thickness of 4 microns or less could be interrogated by the evanescent field. Cladding layers of varying compositions and thickness were thin layered on top. We then layered cladding layers with different refractive indices. A preferred cladding layer would have a refractive index lower than the waveguide material to allow the evanescent wave to take effect. To reduce the reach of the evanescent field, a cladding with a higher refractive index should be used.

In each case fluorescent molecules were bound to the top surface of each cladding layer above the waveguide. We measured the ability of the evanescent wave to excite the bound fluorescent molecules on each cladding layer. It was found that depending on the TIR angle Θ of the light and the thickness of the waveguide, we could adjust the penetration depth of the evanescent field as measured by its ability to excite fluorescent molecules bound to the surface of either the waveguide itself or of any of the cladding layers deposited onto the waveguide. As a consequence, several important uses of the discovered phenomena can be envisioned: interrogation of cell monolayers attached to a waveguide material; diagnostic tests using specific ligands bound to a cladding layer of polymer above the waveguide, as well as targeted analytes bound to the ligands and excited by evanescent energy from the waveguide; multiple layers of cladding materials each having unique properties and/or thickness and each being interrogated by varying evanescent energy from the underlying waveguide.

What is claimed is:

1. A biosensor comprising:
   a top outer layer containing at least one fluid port;
   a fluidics layer below said top outer layer containing at least one fluidics channel in fluid communication with said fluid port;
   a waveguide device below said fluidics layer, wherein said waveguide device comprises:
   a) a first cladding layer below said fluidics layer containing at least one micro-cuvette in fluid communication with said fluidics channel;
   b) a waveguide core layer below said first cladding layer containing at least one channel waveguide core in contact with said micro-cuvette;
   c) a second cladding layer below said waveguide core layer in contact with said waveguide core;
   an excitation light source optically coupled into said waveguide core layer;
   whereby, fluid containing samples having target molecules and optical tags placed in said fluid port is transferred by said fluidics channel into said micro-cuvette where light from said excitation light source enters said micro-cuvette by means of an evanescent wave in said first cladding layer exciting any of said optical tags binding to said target molecules in said micro-cuvette.

2. The laminar biosensor of claim 1 further comprising a plurality of micro-cuvettes in said first cladding layer.

3. The laminar biosensor of claim 1 further comprising a plurality of channel waveguide cores in said waveguide core layer.

4. The laminar biosensor of claim 1 further comprising a bottom supporting layer below said second cladding layer.

5. The laminar biosensor of claim 4 wherein said bottom supporting layer is optically transparent to light produced by said optical tags.

* * * * *